United States Patent
Imamoto et al.

(10) Patent No.: US 7,608,709 B2
(45) Date of Patent: Oct. 27, 2009

(54) 2,3-BIS(DIALKYLPHOSPHINO)PYRAZINE DERIVATIVE, PROCESS OF PRODUCING THE SAME, AND METAL COMPLEX HAVING THE SAME AS LIGAND

(75) Inventors: Tsuneo Imamoto, Chiba (JP); Kazuhiro Yoshida, Chiba (JP); Keitaro Sugita, Chiba (JP)

(73) Assignees: National University Corporation Chiba University, Chiba (JP); Nippon Chemical Industrial Co., Ltd., Tokyo (JP)

( * ) Notice: Subject to any disclaimer, the term of this patent is extended or adjusted under 35 U.S.C. 154(b) by 397 days.

(21) Appl. No.: 11/359,369

(22) Filed: Feb. 23, 2006

(65) Prior Publication Data

US 2007/0021610 A1    Jan. 25, 2007

(30) Foreign Application Priority Data

Jul. 25, 2005   (JP)   ............................ 2005-215003

(51) Int. Cl.
  *C07F 9/535*   (2006.01)
(52) U.S. Cl. ....................... 544/337; 544/229
(58) Field of Classification Search .............. 544/225, 544/337; 514/81
  See application file for complete search history.

(56) References Cited

U.S. PATENT DOCUMENTS

2005/0209455 A1 *  9/2005  Boerner et al. .............. 544/225

FOREIGN PATENT DOCUMENTS

JP          2000-319288 A     11/2000

OTHER PUBLICATIONS

Imamoto et. al. (Tetrahedron Asymmetry, 2005, 17, 560-565).*
Imamoto et. al. (JACS, 2005, 127, 11934-11935 plus cover sheet).*

* cited by examiner

Primary Examiner—Brenda L Coleman
Assistant Examiner—Susanna Moore
(74) Attorney, Agent, or Firm—Smith Patent Office

(57) ABSTRACT

An optically active 2,3-bis(dialkylphosphino)pyrazine derivative represented by formula (1) is disclosed. The pyrazine derivative is preferably a quinoxaline derivative represented by formula (2). In formula (1) and (2), $R^1$ is preferably a t-butyl or adamantyl group, and $R^2$ is preferably a methyl group.

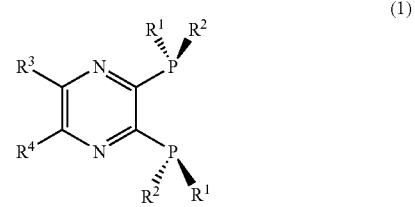

(1)

wherein $R^1$ is a substitutable straight chain or branched alkyl group having 2 to 10 carbon atoms; $R^2$ is a substitutable straight chain or branched alkyl group having fewer carbon atoms than $R^1$; and $R^3$ and $R^4$, which may be the same or different, are each a hydrogen atom or an alkyl group having 1 to 6 carbon atoms, or $R^3$ and $R^4$ are taken together to form a saturated or unsaturated ring.

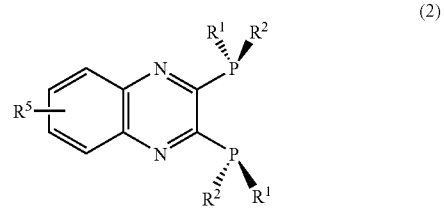

(2)

wherein $R^1$ and $R^2$ are as defined above; and $R^5$ is a monovalent substituent.

7 Claims, No Drawings

2,3-BIS(DIALKYLPHOSPHINO)PYRAZINE DERIVATIVE, PROCESS OF PRODUCING THE SAME, AND METAL COMPLEX HAVING THE SAME AS LIGAND

FIELD OF THE INVENTION

This invention relates to an optically active 2,3-bis(dialkylphosphino)pyrazine derivative and a process of producing the same. The pyrazine derivative is useful as a ligand of a metal complex used as an asymmetric catalyst for asymmetric synthesis. The present invention also relates to a metal complex as an asymmetric synthesis catalyst having the pyrazine derivative as a ligand.

DESCRIPTION OF THE RELATED ART

An optically active phosphine ligand having an asymmetric center on a P atom plays an important role in catalytic asymmetric synthesis reactions using a transition metal complex. In general, nevertheless, the phosphine ligand often involves many reaction steps to prepare a target compound from starting materials. A phosphine is ligand that is synthesized more conveniently than before has therefore been awaited.

Additionally, some of the aforesaid conventional phosphine ligands have insufficient storage stability in air and need care in handling.

The inventors of the present invention previously proposed a 1,2-bis (dialkylphosphino)benzene derivative as an optically active phosphine ligand with an asymmetric center on a P atom (see JP-A-2000-319288). Because the proposed ligand takes on a very stable single chelate conformation with respect to a transition metal, the asymmetric environment surrounding the center metal is efficiently transferred to a substrate. Therefore, transition metal complexes using this ligand, typified by rhodium complexes, are, extremely useful as an asymmetric catalyst for asymmetric hydrogenation. There still has been a demand for a ligand that is easier to synthesize than the benzene derivative and convenient to handle.

SUMMARY OF THE INVENTION

The present invention provides an optically active 2,3-bis (dialkylphosphino) pyrazine derivative represented by formula (1).

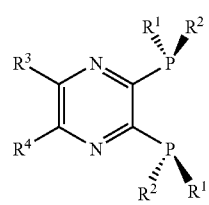

wherein $R^1$ represents a substitutable straight chain or branched alkyl group having 2 to 10 carbon atoms; $R^2$ represents a substitutable straight chain or branched alkyl group having fewer carbon atoms than $R^1$; and $R^3$ and $R^4$, which may be the same or different, each represent a hydrogen atom or an alkyl group having 1 to 6 carbon atoms, or $R^3$ and $R^4$ are taken together to form a saturated or unsaturated ring.

The present invention also provides a preferred process for producing the pyrazine derivative of formula (1). The process includes the steps of:
deprotonating a dialkylphosphine-borane represented by formula (4);
allowing the deprotonated dialkylphosphine-borane to react on a 2,3-dihalogenopyrazine derivative represented by formula (3) to carry out nucleophilic substitution; and then
deboranating the product.

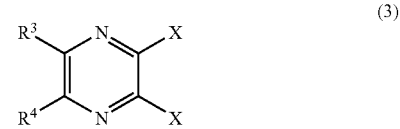

wherein $R^3$ and $R^4$ are as defined above; and X represents a halogen atom.

wherein $R^1$ and $R^2$ are as defined above.

The invention also provides a metal complex as an asymmetric reaction catalyst. The metal complex has the pyrazine derivative of formula (1) as a ligand.

DETAILED DESCRIPTION OF THE INVENTION

In formula (1), $R^1$ represents a substitutable straight-chain or branched alkyl group having 2 to 10 carbon atoms. Examples of $R^1$ include ethyl, isopropyl, n-propyl, isobutyl, n-butyl, sec-butyl, tert-butyl, isoheptyl, n-heptyl, isohexyl, n-hexyl, cyclopentyl, cyclohexyl, and adamantyl. The alkyl group as $R^1$ may be substituted with at least one monovalent substituent. It is preferred for $R^1$ to be a bulky alkyl group causing steric hindrance. From this viewpoint, when $R^1$ is an acyclic alkyl group, a secondary one is preferred to a primary one, and a tertiary one is preferred to a secondary one. It is also preferred that $R^1$ be an alicyclic alkyl group. Preferred alkyl groups as $R^1$ include tert-butyl and adamantyl.

$R^2$ is a substitutable straight-chain or branched alkyl group having fewer carbon atoms than $R^1$. Understandably, the carbon atom number difference between $R^1$ and $R^2$ should be at least one. It is preferred that there be a large difference between $R^1$ and $R^2$ in steric hindrance caused thereby so that the pyrazine derivative of formula (1) may create a highly asymmetric space when used as a ligand of a metal complex catalyst for asymmetric synthesis. In other words, it is preferred that $R^1$ be a bulky group causing higher steric hindrance, while $R^2$ be a less bulky group. Accordingly, a larger difference in carbon atom number between $R^1$ and $R^2$ is preferred. More specifically, the difference in carbon atom number between $R^1$ and $R^2$ is preferably 2 or greater, still preferably 3 or greater, even still preferably 4 or greater. Considering that $R^2$ is a less bulky group, a methyl group could be said to be the most preferred as $R^2$. In general, nevertheless, the group that can be used as $R^2$ is decided relative to $R^1$. Preferred combinations of $R^1$ and $R^2$ include ($R^1$=tert-butyl; $R^2$=methyl) and ($R^1$=adamantyl; $R^2$=methyl).

In formula (1), $R^3$ and $R^4$ are each a hydrogen atom or an alkyl group having 1 to 6 carbon atoms. $R^3$ and $R^4$ may be the same or different. Examples of the alkyl group as $R^3$ and $R^4$ include ethyl, isopropyl, n-propyl, isobutyl, n-butyl, sec-butyl, tert-butyl, isoheptyl, n-heptyl, isohexyl, n-hexyl, cyclopentyl, and cyclohexyl. The alkyl group may appropriately be substituted with one or more monovalent substituents. $R^3$ and $R^4$ may be connected to each other to form a saturated or unsaturated ring, such as a saturated or unsaturated 5- or 6-membered ring including phenyl, cyclohexyl or cyclopentyl. The ring may appropriately be substituted with one or more monovalent substituents.

It is preferred for $R^3$ and $R^4$ to be taken together to form a phenyl group. In that case, the compound of formula (1) is a quinoxaline derivative represented by formula (2).

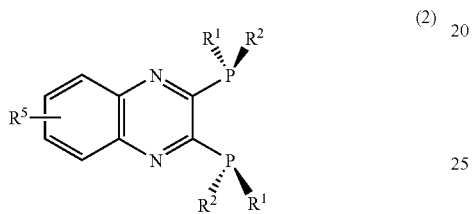

(2)

wherein $R^1$ and $R^2$ are as defined above; $R^5$ represents a monovalent substituent; and n represents an integer of 0 to 4.

In formula (2), the monovalent substituent represented by $R^5$ is not particularly limited and includes a halogen atom.

Specific examples of the 2,3-bis(dialkylphosphino)pyrazine derivative of formula (1) are (R,R)-2,3-bis(tert-butylmethylphosphino)quinoxaline, (R,R)-2,3-bis(adamantylmethylphosphino)quinoxaline, (R,R)-2,3-bis(tert-butylmethylphosphino) pyrazine, and (R,R)-2,3-bis(adamantylmethylphosphino)pyrazine.

The phosphine moieties of the pyrazine derivative of formula (1) have the electron density of the respective P atoms thereof reduced by electron withdrawal by the pyrazine skeleton. As a result, the phosphine moieties are less susceptible to air oxidation, and therefore, the pyrazine derivative of formula (1) has increased storage stability. In particular, the quinoxaline derivative of formula (2) exhibits further improved storage stability because of still less susceptibility to air oxidation.

Furthermore, the pyrazine derivative of formula (1) has high rigidity attributed to the pyrazine skeleton, and the two phosphine moieties form a wide chelating angle with a transition metal. Therefore, a transition metal complex having the pyrazine derivative as a ligand promotes easy progress of reductive elimination. In particular, the quinoxaline derivative of formula (2), a preferred pyrazine derivative of formula (1), provides a transition metal complex catalyst with a wider chelating angle capable of promoting reductive elimination more easily.

A preferred process of producing the 2,3-bis(dialkylphosphino)pyrazine derivative of the invention will then be described. A 2,3-dihalogenopyrazine derivative represented by formula (3), e.g., 2,3-dichloroquinoxaline, is prepared as a starting material. 2,3-Dichloroquinoxaline is commercially available.

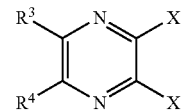

(3)

wherein $R^3$ and $R^4$ are as defined above; and X represents a halogen atom.

Separately, a dialkylphosphine-borane represented by formula (4) is prepared. The process begins with deprotonating the dialkylphosphine-borane of formula (4) in an inert solvent, such as tetrahydrofuran. Deprotonation is carried out by using, for example, butyllithium.

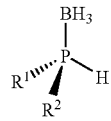

(4)

wherein $R^1$ and $R^2$ are as defined above.

The deprotonated dialkylphosphine-borane is allowed to react on the 2,3-dihalogenopyrazine derivative. Because the electrons of each of the carbon atoms to which a halogen atom is bonded are attracted by the adjacent nitrogen atom, the deprotonated dialkylphosphine-borane, i.e., a nucleophilic reagent attacks, the carbon atoms to cause a nucleophilic substitution reaction. This reaction proceeds rapidly in a liquid nitrogen environment or at room temperature. The reaction results in formation of a diphosphine-borane compound as an intermediate in the reaction system.

Subsequently, the resulting diphosphine-borane compound is deboranated to yield the 2,3-bis(dialkylphosphino) pyrazine derivative of the invention. The deboranation is carried out by adding, for example, N,N,N',N'-tetramethylethylenediamine (hereinafter abbreviated as TMEDA) to the reaction system. The deboranation completes at room temperature in several tens of minutes to several hours. The whole reaction scheme is shown below. It is seen that the reaction mechanism is addition and elimination reaction.

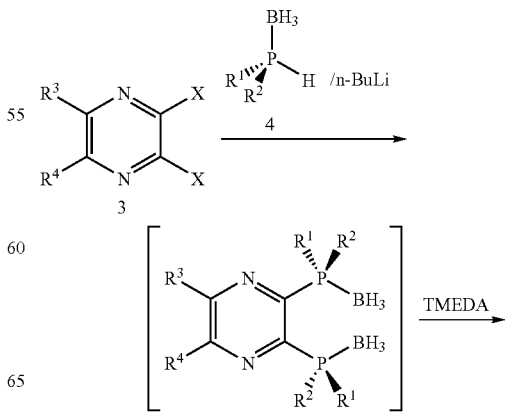

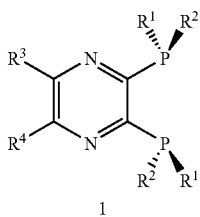

The process offers an advantage that the desired compound can be obtained through a substantially single reaction stage from the starting material. It is noteworthy that the steric configuration with respect to the P atom is retained during the reaction.

The dialkylphosphine-borane used as a nucleophilic reagent is obtainable by known processes including the process disclosed in JP-A-2001-253889.

Specifically, the dialkylphosphine-borane can be prepared as follows. A dialkyl(hydroxymethyl)phosphine-borane represented by formula (5) is dissolved in pyridine at 0° C. to room temperature, and benzoyl chloride is added dropwise to the solution to form a dialkyl(benzoyloxymethyl)phosphine-borane represented by formula (6).

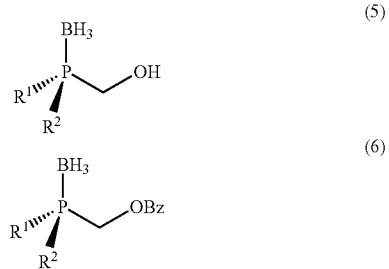

The reaction mixture is diluted with water and extracted with an ether. The organic layer is washed with hydrochloric acid and freed from the solvent to give crystals of the dialkyl (benzoyloxymethyl)phosphine-borane.

The resulting crystals of dialkyl(benzoyloxymethyl)phosphine-borane represented by formula (6) above are dissolved in ethanol, and a potassium hydroxide aqueous solution is dropwise added to the solution to conduct hydrolysis. An aqueous solution containing potassium hydroxide, potassium persulfate, and ruthenium trichloride is then added thereto dropwise to perform reaction. The reaction mixture is neutralized with hydrochloric acid and extracted with an ether. The solvent is removed to yield crystals of a dialkylphosphine-borane of formula (4).

The 2,3-bis(dialkylphosphino)pyrazine derivative of formula (1) coordinates to a transition metal to form a complex. This complex is useful as an asymmetric synthesis catalyst. Asymmetric syntheses include asymmetric hydrogenation, asymmetric 1,4-addition to an electron deficient olefin using an organic boronic acid, asymmetric hydrosilylation, and asymmetric Michael reaction.

The transition metals that can form a complex with the 2,3-bis(dialkylphosphino)pyrazine derivative of the invention include rhodium, ruthenium, iridium, palladium, nickel, and iron. Rhodium is preferred of them. A rhodium complex having the 2,3-bis(dialkylphosphino)pyrazine derivative of formula (1) as a ligand is prepared in accordance with, for example, the process described in The Chemical Society of Japan (ed.), Jikken Kagaku Koza 4th Ed., Maruzen, vol. 18, pp. 327-353. More specifically, the 2,3-bis(dialkylphosphino)pyrazine derivative is reacted with bis(cycloocta-1,5-diene)rhodium tetrafluoroborate to produce a rhodium complex.

Examples of the rhodium complex thus prepared include Rh((S,S)-(1))Cl, Rh(S,S)-(1))Br, Rh((S,S)-(1))I, [Rh((S,S)-(1))(cod)]BF$_4$, [Rh((S,S)-(1)) (cod)]ClO$_4$, [Rh((S,S)-(1)) (cod)]PF$_6$, [Rh((S,S)-(1))(cod)]BPh$_4$, [Rh((S,S)-(1))(ndb)]BF$_4$, [Rh((S,S)-(1))(ndb)]ClO$_4$, [Rh((S,S)-(1)(ndb)]PF$_4$, [Rh((S,S)-(1)(ndb)]BPh$_4$, Rh((R,R)-(1)) Cl, Rh((R,R)-(1))Br, Rh((R,R)-(1))I, [Rh((R,R)-(1))cod)]BF$_4$, [Rh((R,R)-(1)) (cod)]ClO$_4$, [Rh((R,R)-(1)(cod)]PF$_6$, [Rh(R,R)-(1)(cod)]BPh$_4$, [Rh(R,R)-(1))(n)nbd)]BF$_4$, [Rh((R,R)-(1))(ndb)]ClO$_4$, [Rh((R,R)-(1))(ndb)]PF$_6$, [Rh(R,R)-(1))(ndb)]BPh$_4$. Preferred of them is [Rh((S,S)-(1))(cod)]BF$_4$. In the list above, (1) indicates a 2,3-bis(dialkylphosphino) pyrazine derivative of formula (1), and cod, nbd, and Ph stand for 1,5-cyclooctadiene, norbornadiene, and phenyl, respectively.

The present invention will now be illustrated in greater detail with reference to Examples, but it should be understood that the invention is not construed as being limited thereto.

EXAMPLE 1

(a) Synthesis of Compound of Formula (4)

(R)-Tert-butylmethylphosphine-borane (9), a compound represented by formula (4), was synthesized in accordance with the following reaction scheme.

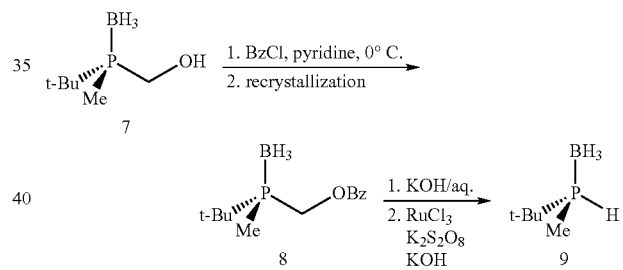

In 10 ml of pyridine was dissolved 2.22 g (15.00 mmol) of (R)-tert-butyl (hydroxymethyl)methylphosphine-borane (7) (92% ee), and 2.1 ml (18 mmol) of benzoyl chloride was added thereto dropwise at 0° C. while stirring. The reaction mixture was heated up to room temperature. One hour later, the reaction mixture was diluted with water and extracted three times with ethyl ether. The organic layer was washed successively with 1 M hydrochloric acid, a sodium hydrogencarbonate aqueous solution, and a saturated sodium chloride aqueous solution and dehydrated over sodium sulfate. The solvent was removed, and the residue was purified by silica gel column chromatography (mobile phase: hexane/ethyl acetate=3/1). The resulting colorless solid was recrystallized twice from a hexane and ethyl acetate mixed solvent to give 2.34 g of optically pure benzoyloxymethyl(tert-butyl)methylphosphine-borane (8) in a yield of 62%.

In 25 ml of ethanol was dissolved 6.05 g (24.0 mmol) of benzoyloxymethyl (tert-butyl)methylphosphine-borane (8) (99% ee), and a solution of 4.0 g (72 mmol) of potassium hydroxide in 15 ml of water was added thereto dropwise to effect hydrolysis, which completed in about one hour. The reaction mixture was diluted with water and extracted three times with ethyl ether. The extract was washed with a saturated sodium chloride aqueous solution and dried over sodium sulfate. The solvent was removed on a rotary evaporator. The residue was purified by silica gel column chromatography (mobile phase: hexane/ethyl acetate=3/1) to give (R)-tert-butyl (hydroxymethyl)methylphosphine-borane (7). The product was dissolved in 72 ml of acetone. Separately, 13.5 g (240 mmol) of potassium hydroxide, 19.4 g (72.0 mmol) of potassium persulfate, and 624 mg (2.4 mmol) of ruthenium trichloride trihydrate were dissolved in 150 ml of water. The acetone solution was slowly added to the aqueous solution (0° C.) while vigorously stirring. Two hours later, the reaction mixture was neutralized with 3 M hydrochloric acid and extracted three times with ethyl ether. The extract was washed with a saturated aqueous solution of sodium chloride and dried over sodium sulfate. The solvent was removed on a rotary evaporator at room temperature. The residue was purified by silica gel column chromatography (mobile phase: pentane/ethyl ether=8/1) to yield 2.27 g (80%) of (R)-tert-butylmethylphosphine-borane (9).

(b) Synthesis of Compound of Formula (1)

(R,R)-2,3-Bis(tert-butylmethylphosphino)quinoxaline (12), a compound of formula (1), was synthesized according to the following reaction scheme.

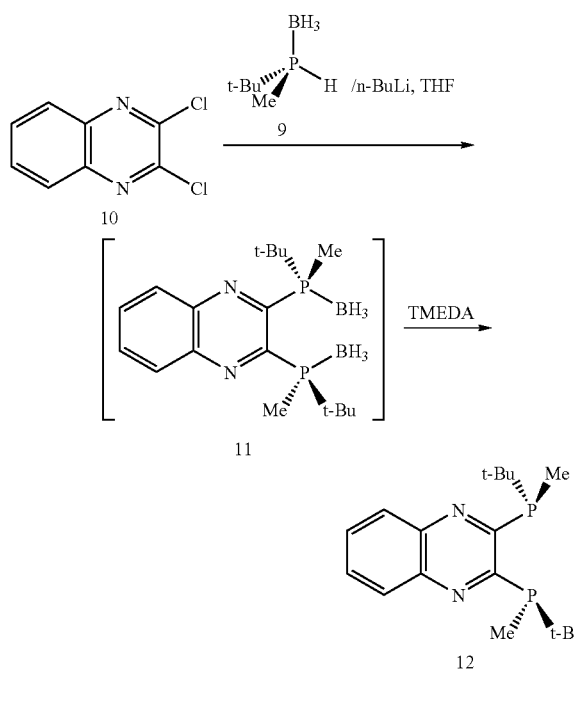

In 4 ml of tetrahydrofuran was dissolved 236 mg (2.0 mmol) of (R)-tert-butylmethylphosphine-borane (9), and the resulting solution was cooled to −78° C. with liquid nitrogen. To the cooled solution was added dropwise 1.25 ml of a 1.6 M hexane solution of n-butyllithium. Fifteen minutes later, a solution of 133 mg (0.67 mmol) of 2,3-dichloroquinoxaline (10) in 4 ml of tetrahydrofuran was added thereto dropwise while vigorously stirring to form a diphosphine-borane compound (11) as an intermediate. The liquid temperature was raised to room temperature over one hour, at which the mixture was stirred for 3 hours. One milliliter of TMEDA was added thereto, and the stirring was continued for an additional 2 hour period to complete deboranation. The reaction was ceased by addition of 1 M hydrochloric acid. The reaction mixture was extracted with hexane. The extract was washed successively with 1 M hydrochloric acid and a saturated sodium chloride aqueous solution and dried over sodium sulfate. The solvent was removed by evacuation, and the residue was purified by silica gel column chromatography (mobile phase: hexane/ethyl acetate=30/1) to give (R,R)-2,3-bis(tert-butylmethylphosphino)quinoxaline (12) as an orange solid. Recrystallization from 1.7 ml of hot methanol gave orange crystals (>99% ee) in a yield of 80%. The physical properties of the product were as follows.

melting point 102-103° C.; $[\beta]^{22}_D$ -54.3(c1.00, CHCl$_3$); $^1$H NMR(395.75 MHz, CDCl$_3$): β 1.00-1.03 (m, 18H), 1.42-1.44 (m, 6H), 7.70-7.74 (m, 2H), 8.08-8.12 (m, 2H); $^{13}$C NMR (99.45 MHz, CDCl$_3$): β 4.77 (t, J=4.1 Hz), 27.59 (t, J=7.4 Hz), 31.90 (t, J=7.4 Hz), 129.50, 129.60, 141.63, 165.12 (dd, J=5.7, 2.4 Hz); $^{31}$P NMR (202.35 MHz, CDCl$_3$): β−17.7(s); IR(KBR) 2950, 1470, 780 cm$^{-1}$; HRMS(FAB) calculated ($C_{18}H_{29}N_2P_2(M^++H)$) 335.1809, observed 335.1826

EXAMPLE 2

Asymmetric Hydrogenation Using Rhodium Complex

Each of the substrates shown in Table 1 below (0.5 mmol) was put into a 50 ml stainless steel reaction tube connected to a hydrogen gas tank. The reaction tube was filled with 1 atm hydrogen (99.9999%, available from Nippon Sanso Corp.). Separately, 1.9 mg (5.0 μmol) of [Rh(nbd)$_2$]BF$_4$ and 2.0 mg (6.0 μmol) of (R,R)-2,3-bis(tert-butylmethylphosphino)quinoxaline (12) were added to 1 ml of degassed methanol, and the mixture was added to the reaction tube with a syringe. The hydrogen gas pressure in the reaction tube was increased to 3 atm. The reaction mixture was evaporated, and the residue was purified by silica gel flash chromatography using ethyl acetate as an eluent. The absolute configuration and the optical purity in terms of percent enantiomer excess (ee) of the resulting product were determined from the retention time in comparison with the standards.

TABLE 1

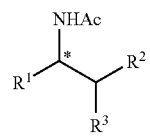

| $R^1$ | $R^2$ | $R^3$ | ee (%)(configuration) |
|---|---|---|---|
| CO$_2$Me | Ph | H | 99.9 (R) |
| CO$_2$Me | 4-AcO-3-MeOC$_6$H$_3$ | H | 99.6 (R) |
| Me | H | CO$_2$Me | 99.7 (R) |
| Me | CO$_2$Me | H | 99.2 (R) |
| Ph | H | H | 99.9 (R) |
| 1-adamantyl | H | H | 96.3 (S) |

EXAMPLE 3

1,4-Addition Reaction of Organic Boronic Acid to β,β-Unsaturated Carbonyl Compound using Rhodium Catalyst To 1 ml of dioxane were added 1.8 mg (9.0 μmol) of [RhCl($C_2H_4$)$_2$]$_2$ and 3.3 mg (9.9 μmol) of (R,R)-2,3-bis(tert-butylmethylphosphino)quinoxaline (12), and the mixture was stirred at room temperature in a nitrogen atmosphere for 15 minutes. To the reaction mixture was added 0.1 ml of a 1.5 M potassium hydroxide aqueous solution, followed by stirring for 15 minutes. To the mixture were added 0.60 mmol of the organic boronic acid shown in Table 2 below and 0.30 mmol of the β,β-unsaturated carbonyl compound shown in Table 2. After the mixture was stirred at 40° C. for 1 hour, a saturated aqueous solution of sodium hydrogencarbonate was added to stop the reaction. The reaction mixture was extracted five times with ethyl ether, and the organic layer was dried over sodium sulfate and concentrated under reduced pressure. The residue was purified by silica gel thin layer chromatography (hexane/ethyl acetate=3/1). The absolute configuration and the percent ee of the products were determined from the retention time in comparison with the standards.

TABLE 2

$R^1\!-\!CH\!=\!CH\!-\!C(O)\!-\!R^2 + ArB(OH)_2 \xrightarrow{\text{Rh/1 (3 mol \%)}}_{\text{KOH, dioxane/H}_2\text{O}} R^1\text{-*CH(Ar)-CH}_2\text{-C(O)-}R^2$

| enone | Ar | Temperature (° C.) | Time (h) | Yield (%)[a] | ee (%) (configuration) |
|---|---|---|---|---|---|
| 5 | Ph | 40 | 1 | 93 | 98.2 (R) |
| 5 | 4-MeOC$_6$H$_4$ | 40 | 1 | 97 | 93.9 (R) |
| 5 | 4-CF$_3$C$_6$H$_4$ | 50 | 12 | 92 | 99.4 (R) |
| 6 | Ph | 50 | 12 | 90 | 96.2 (R) |
| 7 | Ph | 40 | 1 | 97 | 99.1 (S) |

[a]Isolated yield.
enone: 2-cyclohexenone (5), 2-cycloheptenone (6), (E)-5-methyl-3-hexen-2-one (7).

EXAMPLE 4

Asymmetric Ring Opening Reaction Using Palladium Catalyst

To 1 ml of dichloromethane were added 7.1 mg (0.025 mmol) of PdCl$_2$(cod) and 8.3 mg (0.025 mmol) of (R,R)-2,3-bis(tert-butylmethylphosphino)quinoxaline (12), and the mixture was stirred at room temperature in a nitrogen atmosphere for 2 hours. A solution of 0.5 mmol of the oxabenzonorbornadiene compound shown in Table 3 below in 15 ml of dichloromethane was added to the reaction system. To the mixture was further added 0.75 ml of a 1.0 M hexane solution of dimethylzinc or 0.75 ml of a 1.0 M hexane solution of diethylzinc, followed by stirring until the reaction completed. The reaction was ceased by addition of a few drops of water. The reaction mixture was passed through Celite (trade name) and concentrated. The residue was purified by silica gel thin layer chromatography (hexane/ethyl acetate=3/1). The absolute configuration and the percent ee of the products were determined from the retention time in comparison with the standards.

TABLE 3

| $R^1$ | $R^2$ | Time (h) | Yield (%)[a] | ee (%)(configuration) |
|---|---|---|---|---|
| H | Me | 2 | 90 | 95.6 (1S, 2S) |
| H | Et | 15 | 88 | 97.6 (1S, 2S) |
| F | Me | 2 | 90 | 93.8 (1S, 2S) |

[a]Isolated yield.

As described above, the pyrazine derivative of the present invention is stable in air and therefore has very good handling properties including storage stability. According to the process of the present invention, the pyrazine derivative can easily be produced. The pyrazine derivative functions as a ligand to provide a metal complex that catalyzes various asymmetric syntheses with high enantiomer selectivity and reaction activity.

What is claimed is:

1. An optically active 2,3-bis(dialkylphosphino)pyrazine represented by formula (1):

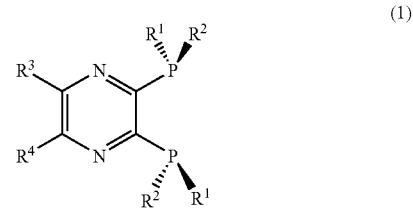

wherein $R^1$ represents a straight chain or branched alkyl group having 2 to 10 carbon atoms and the alkyl group of $R^1$ may be substituted with at least one monovalent substituent;

$R^2$ represents a substituted or unsubstituted straight chain or branched alkyl group having fewer carbon atoms than $R^1$;

and $R^3$ and $R^4$, which may be the same or different, each represent a hydrogen atom or an alkyl group having 1 to 6 carbon atoms, or $R^3$ and $R^4$ are taken together to form a saturated or unsaturated ring.

2. The pyrazine of claim 1, which is represented by formula (2):

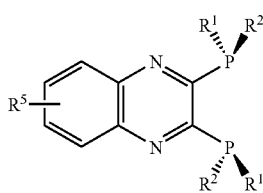

(2)

wherein $R^1$ and $R^2$ are as defined in claim 1, and $R^5$ represents a monovalent substituent.

3. A process for producing the pyrazine of claim 1, comprising the steps of:
deprotonating a dialkylphosphine-borane represented by formula (4);
allowing the deprotonated dialkyiphosphine-borane to react with a 2,3-dihalogenopyrazine represented by formula (3) to carry out nucleophilic substitution; and then deboranating the product:

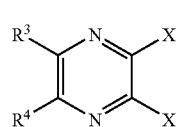

(3)

wherein $R^3$ and $R^4$ are as defined in claim 1; and X represents a halogen atom:

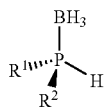

(4)

wherein $R^1$ and $R^2$ are as defined in claim 1.

4. pyrazine of claim 1, wherein the pyrazine is used as a ligand of a metal complex catalyst for asymmetric synthesis.

5. An optically active 2,3bis(dialkylphosphino)pyrazine represented by formula (1):

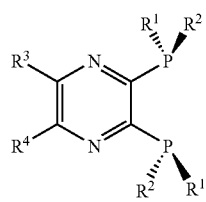

(1)

wherein $R^1$ is a tert-butyl group or an adamantyl group; $R^2$ is a methyl group; and $R^3$ and $R^4$, which may be the same or different, each represent a hydrogen atom or an alkyl group having 1 to 6 carbon atoms, or $R^3$ and $R^4$ are taken together to form a saturated or unsaturated ring.

6. The pyrazine according to claim 5, wherein the pyrazine represented by formula (1) is one of (R,R)-2,3-bis(tert-butylmethylphosphino)quinoxaline, (R,R)-2, 3-bis(adamantylmethylphosphino)quinoxaline, (R,R)-2,3-bis(tert-butylmethylphosphino)pyrazine, and (R,R)-2,3-bis(adamantylmethylphosphino)pyrazine.

7. An optically active 2,3-bis(dialkylphosphino)pyrazine represented by formula (1):

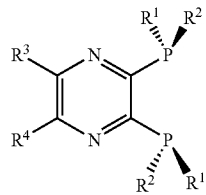

(1)

wherein $R^1$ represents a straight chain or branched alkyl group having 2 to 10 carbon atoms; $R^2$ represents a straight chain or branched alkyl group having fewer carbon atoms than $R^1$; and $R^3$ and $R^4$, which may be the same or different, each represent a hydrogen atom or an alkyl group having 1 to 6 carbon atoms, or $R^3$ and $R^4$ are taken together to form a saturated or unsaturated ring.

* * * * *